United States Patent [19]
Raab

[11] Patent Number: 5,073,651
[45] Date of Patent: Dec. 17, 1991

[54] PROCESS FOR THE PREPARATION OF EXTENSIVELY FLUORINATED ALKYL BROMIDES

[75] Inventor: Klaus Raab, Burgkirchen, Fed. Rep. of Germany

[73] Assignee: Hoechst Aktiengesellschaft, Frankfurt am Main, Fed. Rep. of Germany

[21] Appl. No.: 604,872

[22] Filed: Oct. 26, 1990

[30] Foreign Application Priority Data

Nov. 11, 1989 [DE] Fed. Rep. of Germany ....... 3937567

[51] Int. Cl.$^5$ .............................................. C07C 17/20
[52] U.S. Cl. ................................................... 870/170
[58] Field of Search ................................. 570/170, 174

[56] References Cited

U.S. PATENT DOCUMENTS 2,678,953  5/1954  Conly .
2,875,253  2/1959  Barnhart .

FOREIGN PATENT DOCUMENTS 49-48286  12/1974  Japan .................................. 570/170
0184033   9/1985  Japan .................................. 570/170

OTHER PUBLICATIONS

Haszeldine, R. N., J. Chem. Soc.: 3761–3768 (1953).
Long, D. M. et al., *Preparation Properties and Industrial Applications of Organofluorine Compounds*, New York, John Wily and Sons, 1982, p. 154.
Huang, B. et al., *Chem. Abs.* 102:78312x (1985).
Furutaka, Y. et al., *Chem. Abs.* 104:88106p (1986).

*Primary Examiner*—Alan Siegel

[57] ABSTRACT

A process for the preparation of extensively fluorinated alkyl bromides from the corresponding iodides is described in which, in a dipolar aprotic solvent, a bromide which is present as a salt of an alkali metal, alkaline earth metal, copper or substituted or unsubstituted amonium is reacted with an extensively fluorinated alkyl iodide at 120° to 200° C. The reaction can be carried out at −10° to +120° C., in some cases with improved yields if it is carried out in the presence of an alkali metal salt of at least one hydroxyalkanesulfinic acid having 1 to 5 carbon atoms. The novel process enables uncomplicated apparatuses to be used without particular safety measures and presents no corrosion problems.

9 Claims, No Drawings

PROCESS FOR THE PREPARATION OF EXTENSIVELY FLUORINATED ALKYL BROMIDES

DESCRIPTION

The invention relates to a process for the preparation of extensively fluorinated alkyl bromides from alkyl iodides.

It is known from U.S. Pat. No. 2,678,953 that perfluoroalkyl bromides can be obtained from the dry metal salts of perfluoroalkylcarboxylic acids by reaction with bromine, the use of visible light increasing the conversion. The preferred silver salt is used in the only example. This process is expensive because the perfluoroalkylcarboxylic acid must first be produced, for example by the known reaction of perfluoroalkyl iodide with $SO_3$ or fuming sulfuric acid. The acid must then be converted into the metal salt and this must be dried. Reaction with toxic and caustic bromine furthermore requires particular caution and an increased expenditure on apparatus (safety measures, corrosion). One $CF_2$ group of the perfluoroalkyl iodide is moreover lost during the reaction chain.

It is furthermore known from U.S. Pat. No. 2,875,253 that a lower hydrocarbon substituted with fluorine, bromine and optionally with chlorine can be telomerized as a telogen with a fluorine-containing olefin, which can additionally contain chlorine atoms, in the presence of a peroxidic polymerization promoter. Possible telogens which are mentioned are, inter alia, $CF_3Br$, $CF_2BrCl$, $CF_2Br_2$, $C_2F_4BrCl$, $C_3F_6BrH$ and $C_3F_6Br_2$, and amongst a large number of possible fluorine-containing olefins, tetrafluoroethylene is mentioned. The reaction of these compounds would have to lead to extensively fluorinated alkyl bromides in the sense of the present invention, but there is no example from which the precise conditions under which and with what success the reaction with tetrafluoroethylene can be carried out could be seen. $CF_2=CFCl$ is always used as the fluorine-containing olefin in the examples.

In a paper by Long. Higgins, Mattrey, Mitten and Multer on radiopaque fluorohydrocarbons (R. E. Banks, "Preparation, Properties and Industrial Applications of Organofluorine Compounds", 1982, Ellis Horwood Ltd. Publishers/Chichester, pages 139 to 156), at the end of the remarks (page 154, bottom) it is mentioned that the perfluoro-n-hexyl bromide and perfluoro-iso-heptyl bromide used for the investigations was produced by thermal bromination of the corresponding perfluoroalkyl iodides with elemental bromide, but further details are lacking. The apparatus difficulties already mentioned above without doubt increase when bromine is used if these aggressive substances are subjected to thermal processes, i.e. at higher temperatures.

R. N. Haszeldine, J. Chem. Soc., 1953, pages 3,761 to 3,768 and Huang Bingnan and Huang Weiyuan, Shanghai Inst. Org. Chem. Acad. Sinica, Huaxue Xuebao 42, pages 1,106 to 1,108 (C.A. 102; 78312×), 1984 describe photochemical bromination of perfluoroalkyl iodides [Examples:$R_fI$ or $Cl(CF_2)_4I$] with bromine under UV radiation. $R_fBr$ or $Cl(CF_2)_4Br$ is obtained in a very good yield after a reaction of 168 or 50 hours respectively. Nevertheless, this process is also expensive in terms of apparatus and energy.

Finally, it is known from Japanese Preliminary Published Specification 60-184033-A2, 1985 (C.A. 104; 88106p) that $C_nF_{2n+1}Br$ (n=6 to 11) can be produced by reaction of $C_nF_{2n+1}I$ with bromine in the presence of a compound which generates free radicals (for example azodiisobutyronitrile). $C_6F_{13}Br$ is thus obtained in a yield of 40%. The use of elemental bromine also requires apparatus measures here.

The object of the present invention is to provide a process which enables production of perfluoroalkyl bromides using substances which are considerably less toxic, hazardous and corrosive by comparison.

The novel process for the preparation of extensively fluorinated alkyl bromides from compounds of the formula $$X-(CF_2)_n-I \quad (I)$$

in which: X is H, F, Cl, Br, I or $(CF_3)_2CF-$ and n is 1 to 16 comprises reacting, in at least one dipolar aprotic solvent, 1 mol of bonded iodine atom of the compound of the formula (I) with 1 to 4 mol of bromide ions which are present as salts with at least one of the following cations: alkali metal, alkaline earth metal, copper or substituted or unsubstituted ammonium, at 120° to 200° C. under normal atmospheric pressure or under the autogenous pressure of the reaction mixture.

Compounds of the abovementioned formula (I) can be prepared by various known processes. For example, perfluoroethyl iodide can be produced by reaction of iodine with iodine pentafluoride and tetrafluoroethylene, and this can in turn be reacted with further tetrafluoroethylene by telomerization to give higher perfluoroalkyl iodides. Analogous compounds are obtainable by using corresponding starting substances. Some of the compounds of the formula (I) are commercial products.

Those compounds of the formula (I) in which X is I, and in particular those in which X is either $(CF_3)_2CF-$ or F, are preferably used. Compounds of the formula (I) in which n is greater than 16 in general result in longer reaction times and often poorer yields, and they are also as a rule less readily usable. Compounds of the formula (I) in which n is 4 to 12 and in particular 6 to 8 are preferred because they are readily usable. It is also possible to employ mixtures of compounds of the formula (I) which contain different substituents X and/or have different indices n.

According to the invention, 1 mol of bonded iodine atom of the compound of the formula (I) is reacted with 1 to 4 mol of bromide ions, which can be present as salts with various cations. If less than 1 mol of bromide ion is used per mol of iodine atom in the compound of the formula (I), poorer yields are obtained. More than 4 mol of bromide ions can on principle be employed per mol of iodine atom in the compound of the formula (I), but in general no improvement in yield is observed in this procedure, so that this is an unnecessary expense. Preferably, 1.1 to 2 mol of bromide ions are used per mol of iodine atom in the compound of the formula (I).

The bromide can be present as the salt of substituted or unsubstituted ammonium; examples of possible substituents on the nitrogen of the ammonium are alkyl groups having 1 to 4 carbon atoms or hydroxyalkyl groups having 2 to 4 carbon atoms. The bromide can furthermore be present as a salt with copper or an alkaline earth metal, for example calcium or magnesium, or as a salt with an alkali metal. The bromides of lithium, sodium and potassium are preferred because they are easy to obtain and give favorable results.

The reaction of the compound of the formula (I) with the bromide is carried out in a dipolar aprotic solvent. 0.1 to 20 cm³ of solvent are used per g of the compound of the formula (I) in this reaction. These limits are not critical, and it is also possible, for example, to employ more than 20 cm³ of solvent per g of compound of the formula (I), but it is in general sufficient to choose an amount of solvent which lies within the range stated, and preferably 0.5 to 10 cm³ of solvent are used per g of compound of the formula (I). Suitable dipolar aprotic solvents are, for example, N-methylpyrrolidone, dimethyl sulfoxide or tetramethylene sulfone, dialkylcarboxylic acid amides and in particular dimethylformamide or dimethylacetamide preferably being employed. It is also possible to use mixtures of various dipolar aprotic solvents.

The reaction according to the invention described above is carried out at a temperature of 120° to 200° C., and advantageously takes place under normal atmospheric pressure or under the autogenous pressure of the reaction mixture. The use of higher pressures is as a rule not required and represents an unnecessary expense. The reaction in general proceeds too slowly below 120° C., and above 200° C. the formation of undesirable by-products is increasingly found. If the reaction is to be carried out in the upper temperature range, for example from 160° to 200° C., dimethylacetamide is advantageously used instead of dimethylformamide. The reaction is preferably carried out at temperatures of 130° to 180° C.

The reaction time depends on the temperature applied and the starting substances employed and is in general 1 to 20 hours; longer reaction times are possible, but usually no additional effect which would justify the ever worsening space-time yields is observed. Good results are often obtained over a reaction time of 2 to 10 hours.

The reaction according to the invention is advantageously carried out with exclusion of oxygen in an inert gas, for example nitrogen or argon.

When the reaction has ended, the mixture can be worked up in various ways, for example by steam distillation or by cooling to room temperature, adding water and separating off the phase which contains the organic substances. In both cases, the resulting mixture of organic substances can advantageously be subjected, after drying with a customary drying agent, to fractional distillation at bottom temperatures of up to a maximum of about 200° C., reduced pressure being applied if necessary.

It has furthermore been found that the reaction described above can be carried out at a lower temperature, in some cases giving better yields, in the presence of an alkali metal salt of at least one hydroxyalkanesulfinic acid having 1 to 5 carbon atoms. A hydroxyalkanesulfinic acid having 1 to 3 carbon atoms is preferably used, and the sodium or potassium salts are preferably employed as the alkali metal salts. Particularly good results are obtained with the sodium salt of hydroxymethanesulfinic acid.

In the case of the reaction in the presence of hydroxyalkanesulfinates, 0.2 to 20 mol of these, preferably 0.5 to 1.5 mol, are used per mol of bonded iodine atom in the compound of the formula (I). The reaction temperature depends on the starting substances employed and is −10° to 120° C. Below −10° C., the reaction in general proceeds too slowly, above +120° C. undesirable side reactions increase, and the reaction is preferably carried out at temperatures of 0° to +40° C. The statements made above apply to the pressure. The alkali metal salt of the hydroxyalkanesulfinic acid is advantageously employed as a powder or as a suspension in the abovementioned solvents, the amount of solvent advantageously being chosen so that the batch remains readily stirrable.

It has been found to be advantageous not to add all the intended alkali metal salt of the hydroxyalkanesulfinic acid at the start of the reaction, but to add only some and to add the remainder continuously or batchwise (in portions) during the course of the reaction.

As already mentioned above, the reaction time depends on the reaction temperature chosen and the starting substances; because of the lower reaction temperature, it is in general longer than in the process described above in which no alkali metal salt of the hydroxyalkanesulfinic acid is used. If this salt is used, the reaction time is in general 5 to 100 hours, good results often being obtained in the range from 7 to 50 hours. Working up to give the extensively fluorinated alkyl bromides and any necessary purification are carried out as described above.

The extensively fluorinated alkyl bromides produced by the process according to the invention can be employed in the medical sector, such as, for example, as contrast media in examinations using X-rays or ultrasound, for example for visualizing tumors, for organ perfusion and in aqueous emulsion as a blood substitute. Further uses of the extensively fluorinated alkyl bromides are high temperature inert liquids and contrast media for $^{19}F$-nuclear magnetic resonance spectrum (NMR) analysis.

In contrast to the known processes, the process according to the invention makes it possible to carry out the reaction in less expensive apparatuses without difficulties in respect of corrosion and particular safety measures. The novel process gives rise to by-products which can be isolated by the customary route and have various uses, for example the compounds which carry a hydrogen atom instead of the iodine atom in the abovementioned formula (I) can be used as heat transfer liquids, and compounds which carry a —COOH group instead of the —CF$_2$I group in the abovementioned formula (I), or salts thereof, are employed, for example, as chemically stable emulsifiers.

The following examples are intended to illustrate the invention in more detail.

EXAMPLE 1

54.6 g (0.1 mol) of 1-iodo-perfluorooctane and 15.4 g (0.15 mol) of anhydrous sodium bromide are weighed into a round-bottomed flask of 500 cm³ capacity, which is equipped with an internal thermometer and a glass stirrer, and after addition of 50 cm³ of dimethylacetamide the mixture is heated to 156° C. in a nitrogen atmosphere, while stirring. 0.15 mol of bromide ions per mol of bonded iodine atom in the 1-iodo-perfluorooctane [=compound of the formula (I)] and 0.92 cm³ of dipolar aprotic solvent per g of compound of the formula (I) are employed. The temperature falls to 142° C. during a reaction time of 6 hours, the reaction mixture is then cooled to room temperature, water is added to the contents of the flask and the mixture is introduced into a separating funnel. A liquid lower organofluorine phase separates out in this. This lower phase is extracted by shaking with an aqueous solution containing 20% by weight of NaOH and then with water and dried. 47.4 g of a crude product, which is analyzed by $^{19}$F-NMR spectroscopy, are obtained. The yields, based on the 1-iodo-perfluorooctane employed, are: 29% of 1-bromo-perfluorooctane; 17% of 1-hydro-perfluorooctane and 48% of the starting substance 1-iodo-perfluorooctane.

EXAMPLE 2

The procedure is as described in Example 1, but 13 g (0.15 mol) of lithium bromide are employed instead of the sodium bromide and dimethylformamide is employed instead of the dimethylacetamide. The molar ratios of the compound of the formula (I) to bromide and to cm$^3$ of solvent remain the same. The reaction mixture is heated to 158° C., the temperature falls to 133° C. over 6 hours and the mixture is then cooled and worked up as described in Example 1. 47.5 g of crude product, which is analyzed by $^{19}$F-NMR spectroscopy, are obtained. The yields, based on the 1-iodo-perfluorooctane employed, are: 38% of 1-bromo-perfluorooctane; 9% of 1-hydro-perfluorooctane and 45% of the starting substance 1-iodo-perfluorooctane.

EXAMPLE 3

The procedure is as described in Example 1, but 21.5 g (0.15 mol) of copper(I) bromide are used instead of the sodium bromide and 100 cm$^3$ of dimethylformamide are used instead of the 50 cm$^3$ of dimethylacetamide. 1.5 mol of bromide ions per mol of bonded iodine atom in the compound of the formula (I) and 1.83 cm$^3$ of polar aprotic solvent per g of compound of the formula (I) are used. The mixture is heated to 138° C., while stirring, and the temperature falls to 129° C. over 14 hours. The mixture is then cooled and filtered under reduced pressure, an intermediate cold trap being used, and the filtrate is worked up as described in Example 1. 38.0 g of crude product, which is analyzed by $^{19}$F-NMR spectroscopy, are obtained. The yields, based on the 1-iodo-perfluorooctane employed, are: 32% of 1-bromo-perfluorooctane; 7.6% of 1-hydro-perfluorooctane and 34% of the starting substance 1-iodo-perfluorooctane.

EXAMPLE 4

The procedure is as described in Example 1, but 100 cm$^3$ of dimethylformamide are used instead of the 50 cm$^3$ of dimethylacetamide, and 15.4 g of dihydrate of the sodium salt of hydroxymethanesulfinic acid (a commercially available product) are additionally used. 1.5 mol of bromide ions and 1 mol of dihydrate of the sodium salt of hydroxymethanesulfinic acid per mol of bonded iodine atom in the compound of the formula (I) and 1.83 cm$^3$ of polar aprotic solvent per g of compound of the formula (I) are used. The reaction mixture is cooled to +10° C., while stirring, and is kept at this temperature for 14 hours. At the end of the reaction time, the mixture is warmed to room temperature and worked up as described in Example 1, the organofluorine phase separating out only slowly in the separating funnel after the mixture has been left to stand for several hours. 34.5 g of crude product, which is analyzed by $^{19}$F-NMR spectroscopy, are thus obtained. The yields, based on the 1-iodo-perfluorooctane employed, are: 48% of 1-bromo-perfluorooctane; 1% of 1-hydroperfluorooctane and 18.5% of the starting substance 1-iodo-perfluorooctane.

EXAMPLE 5

The procedure is as described in Example 4, but 41.2 g (0.4 mol) of sodium bromide are employed this time instead of the 15.4 g of sodium bromide and 300 cm$^3$ of dimethylformamide are employed this time instead of the 100 cm$^3$ of dimethylformamide. The amount of dihydrate of the sodium salt of hydroxymethanesulfinic acid added remains the same. 4 mol of bromide ions and 1 mol of dihydrate of the sodium salt of the hydroxyalkanesulfinic acid per mol of bonded iodine atom in the compound of the formula (I) and 5.49 cm$^3$ of polar aprotic solvent per g of compound of the formula (I) are used. The reaction mixture is stirred at room temperature (25° C.) for 6 hours and then worked up as described in Example 1, the organofluorine phase again settling only slowly after several hours in the separating funnel. 39.4 g of a crude product, which is analyzed by $^{19}$F-NMR spectroscopy, are obtained. The yields, based on the 1-iodo-perfluorooctane employed, are: 40% of 1-bromo-perfluorooctane; 3% of 1-hydro-perfluorooctane and 33% of the starting substance 1-iodo-perfluorooctane.

EXAMPLE 6

54.6 g (0.1 mol) of 1-iodo-perfluorooctane and 20.6 g (0.2 mol) of anhydrous sodium bromide are introduced into a round-bottomed flask of 1 dm$^3$ capacity, which is equipped with an internal thermometer and a glass stirrer, and after addition of 500 cm$^3$ of dimethylformamide, the mixture is stirred under a nitrogen atmosphere, the temperature of the contents of the flask being kept at 0° C. for 48 hours using a cryostatic temperature regulator. At the start of the reaction —after 8 hours, after 24 hours and after 32 hours—in each case 7.7 g (0.05 mol) of dihydrate of the sodium salt of hydroxymethanesulfinic acid are added in four equal portions. After 48 hours, the reaction mixture is heated to room temperature, water is added and the mixture is worked up as described in Example 1. Only slow settling of the organofluorine phase in the separating funnel is again observed. One possible reason for this is the perfluorooctanoic acid which is also formed in the reaction and acts as an emulsifier. 31.0 g of a crude product which, according to analysis by $^{19}$F-NMR spectroscopy and gas chromatography, contains 94% by weight of 1-bromo-perfluorooctane; 2% by weight of 1-hydroperfluorooctane and 1.5% by weight of the starting substance 1-iodo-perfluorooctane are obtained. —2 mol of bromide ions and 2 mol of dihydrate of the sodium salt of hydroxymethanesulfinic acid per mol of bonded iodine atom in the compound of the formula (I) and 9.16 cm$^3$ of polar aprotic solvent per g of compound of the formula (I) are employed.

EXAMPLE 7

273 g (0.5 mol) of 1-iodo-perfluorooctane, 102.9 g (1 mol) of anhydrous sodium bromide and 1000 cm$^3$ of dimethylformamide are introduced into a round-bottomed flask of 2 dm$^3$ capacity, which is equipped with an internal thermometer and glass stirrer. The contents of the flask are flushed with nitrogen, while stirring, and kept at a temperature of 15° C. throughout the entire reaction time of 48 hours. At the start of the reaction—after 8 hours and after 24 hours—in each case 38.5 g portions (0.25 mol each) of dihydrate of the sodium salt of hydroxymethanesulfinic acid are added. At the end of the reaction time, the contents of the flask are warmed to room temperature, 1 dm³ of water is added and the mixture is brought to pH 11 with an aqueous solution containing 30% by weight of NaOH. The contents of the flask are now subjected to steam distillation (bottom temperature 99° to 108° C., transition temperature 92° to 102° C.), until no further lower organofluorine phase separates out in the receiver. The water distilled off from the bottom product is replaced by a dropping funnel. The lower organofluorine phase in the distillation receiver is separated off from the upper aqueous phase in a separating funnel and then stirred at 95° C. with an aqueous solution containing 20% by weight of NaOH, subsequently extracted by shaking with water and dried. 166 g of a crude product which, according to analysis by gas chromatography, contains 87.1% of 1-bromo-perfluorooctane and 10.9% of 1-hydro-perfluorooctane are obtained. This corresponds to a crude product yield of 58% of 1-bromo-perfluorooctane. 160 g of this crude product are distilled in a split tube column under normal atmospheric pressure. 93 g of 1-bromo-perfluorooctane of boiling point 140° to 141° C. are obtained as the main runnings. Taking into account that not all the crude product was used for the distillation, this corresponds to a yield of 39%, based on the 1-iodo-perfluorooctane employed. Further 1-bromo-perfluorooctane can also be obtained by a second distillation of the distillation first runnings and residues. —2 mol of bromide ions and 1.5 mol of the dihydrate of the sodium salt of hydroxymethanesulfinic acid per mol of bonded iodine atom in the compound of the formula (I) and 3.66 cm³ of polar aprotic solvent per g of compound of the formula (I) are employed.

I claim:

1. A process for the preparation of an extensively fluorinated alkyl bromide from a compound of the formula $$X-(CF_2)_n-I \qquad (I)$$

in which: X is H, F, Cl, Br, I or $(CF_3)_2CF-$ and n is 1 to 16, comprising: reacting, in at least one dipolar aprotic solvent, 1 mol of bonded iodine atom of the compound of the formula (I) with 1 to 4 mol of bromide ions which are present as salts with at least one of the following cations: alkali metal, alkaline earth metal, copper or substituted or unsubstituted ammonium, at 120° to 200° C. under normal atmospheric pressure or under the autogenous pressure of the reaction mixture so that the iodine in the compound of formula (I) is replaced partly by bromine.

2. The process as claimed in claim 1, wherein the reaction is carried out in the presence of 0.2 to 2 mol of an alkali metal salt of at least one hydroxyalkanesulfinic acid having 1 to 5 carbon atoms per mol of bonded iodine atom of the compound of the formula (I) at a temperature of $-10°$ to $+120°$ C.

3. The process as claimed in claim 2, wherein the alkali metal salt of the hydroxyalkanesulfinic acid is added to the reaction mixture continuously or batchwise during the reaction.

4. The process as claimed in claim 1, wherein at least one perfluoroalkyl iodide having 4 to 12 carbon atoms is employed.

5. The process as claimed in claim 1, wherein lithium bromide, sodium bromide or potassium bromide is employed.

6. The process as claimed in claim 1, wherein dimethylformamide or dimethylacetamide or a mixture thereof is employed as the solvent.

7. The process as claimed in claim 1, wherein the reaction is carried out at a temperature of 130° to 180° C.

8. The process as claimed in claim 2, wherein the reaction is carried out at a temperature of 0° to 40° C.

9. The process as claimed in claim 1, wherein 0.1 to 20 ccm of solvent are used per g of compound of the formula (I).

* * * * *